(12) United States Patent
Woodbridge

(10) Patent No.: US 6,203,710 B1
(45) Date of Patent: Mar. 20, 2001

(54) LIQUID DECONTAMINATION METHOD AND APPARATUS

(76) Inventor: David D. Woodbridge, 10805 N. 53rd St., Tampa, FL (US) 33617-3619

( * ) Notice: Subject to any disclaimer, the term of this patent is extended or adjusted under 35 U.S.C. 154(b) by 0 days.

(21) Appl. No.: 09/255,414

(22) Filed: Feb. 22, 1999

(51) Int. Cl.[7] .................................. C02F 1/48; C02F 1/72
(52) U.S. Cl. .................... 210/695; 210/198.1; 210/223; 210/243; 210/294; 210/748; 210/758; 210/759; 210/760; 210/764; 204/155; 204/554; 204/557; 204/660; 204/664; 204/672; 204/673; 95/28; 95/57; 96/3
(58) Field of Search .................................. 210/222, 243, 210/695, 748, 220, 198.1, 206, 758, 759, 760, 764; 204/155, 554, 557, 660, 664, 672, 673; 96/3; 95/28, 57

(56) References Cited

U.S. PATENT DOCUMENTS 3,722,677 * 3/1973 Lehnert ............................... 96/3
4,248,707 * 2/1981 Granger ............................... 210/695
5,304,302 * 4/1994 Bossert ............................... 210/222

* cited by examiner

Primary Examiner—David A. Reifsnyder
(74) Attorney, Agent, or Firm—William M. Hobby, III

(57) ABSTRACT

A liquid decontamination system has a liquid treatment chamber having a liquid input and output and a gas input and output. A plurality of electrodes are positioned to place a voltage across the liquid treatment chamber and the liquid therein. A plurality of magnets are also positioned adjacent the electrodes for placing a magnetic field across the chamber and liquid therein. As the contaminated liquid is fed through the liquid treatment chamber, a predetermined gas, such as nitrogen, ozone, oxygen, or hydrogen peroxide, are fed into the contaminated liquid while simultaneously having the electric and magnetic fields applied to the liquid. The liquid leaving the treatment chamber is fed to a flush tank which removes contaminates and agglomerated solids therefrom.

14 Claims, 1 Drawing Sheet

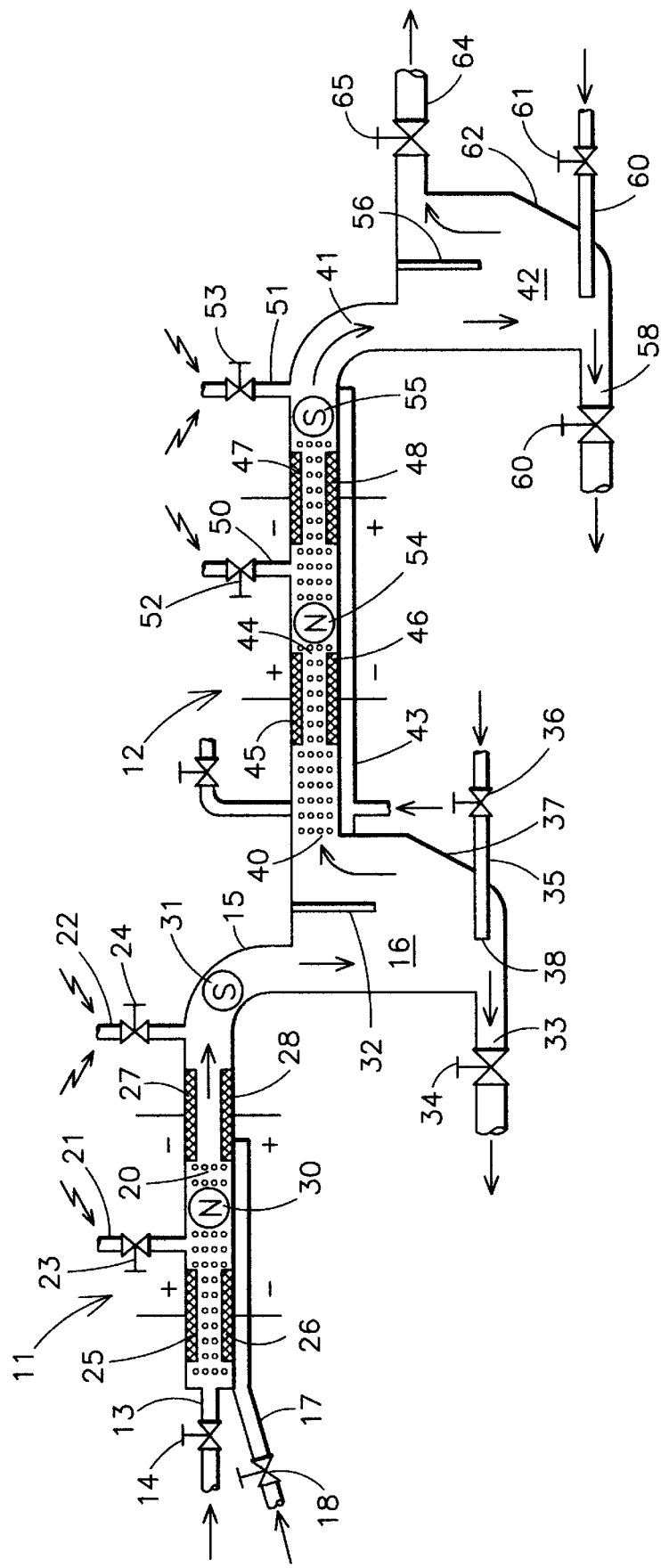

LIQUID DECONTAMINATION METHOD AND APPARATUS

BACKGROUND OF THE INVENTION

The present invention relates to an apparatus and method for the decontamination of liquids and especially to a method and apparatus of decontaminating liquids using separate and combined electric and magnetic fields in combination with a selected gas injected into the liquid as it passes through the electric and magnetic fields.

Clean water and other types of fluids are essential to human life and industrial operations. One area of particular concern is the prevention of both microbial and chemical contamination of dental and medical waters. Clean water for household use is also a vital necessity. Many industries require ultra clean water and other fluids for their operations. Zoos, and animal hospitals, doctors and caretakers need clean water to assure the health of their wards.

A severe problem exits due to both microbial and chemical adherence to the interior surfaces of water feed lines and tubing. The formation of a highly protective biofilm layer provides ideal growth conditions for microbiological organisms and the accumulation of chemical contamination. Slime accumulation within fluid feed lines and tubing provides an ideal environment for water contamination. Exposure to Pseudomonas, Moraxella, Staphylococcus, and Legionella has been linked to medical and dental water. Potential exposures of people to these same microorganisms exists in household water systems.

Present methods of chlorination of water at large water treatment facilities kills chloroform bacteria within the treatment plant. However, many bacteria are not affected by the chlorination and the method does nothing to decrease chemical contaminants. In fact, chlorination increases chemical contamination of water by creating chlorinated organics, such as the trihalomethanes. Even the effectiveness of chlorine to kill bacteria decreases with time after it is placed in the water. Thus, locations close to a water treatment facility have over chlorinated water and locations miles from the facility have little or no effective bactericide in their water.

A methodology has been developed and tested that will both kill micro-organisms and reduce many chemical contaminants in both water and other fluids. The present invention deals with a system of independent electric and magnetic fields in the presence of certain gases or agents and has been shown to notably reduce bacteria and other micro-organisms and simultaneously remove many chemicals from liquids. The method has been tested and shown to eliminate bacteria as well as chemicals from water flowing through a combination of electric and magnetic fields.

The present system combines the effects of electric and magnetic fields being placed across polluted water which has had predetermined gases fed therein. The electric field polarizes the molecules upon which its acts. This polarization disrupts the organic molecular action. Motion of these polarized molecules, both organic and inorganic, through a magnetic field produces a circular or turbulent motion that causes agglomeration into heavier particles. These particles are separated by gravity such that the cleaner fluid is above the fluid concentrated by the contaminated particles. Removing the lower contaminated fluid leaves a cleaner liquid.

Another important affect of the electric field is the creation of hydroxyl ions within the fluid. Recent attention has been given to the action of the hydroxyl radical and its role in the purification of water. Phenols and creosols react rapidly with the hydroxyl radical. A stoichiometric model for an Advanced Oxidation Process has been developed that is based on the fact that organic radicals, created by hydroxyl radicals, attack organic contaminants and react quickly with oxygen to form peroxy radicals. Then, these peroxy radicals can either eliminate super oxides to become stable by-products or undergo more complicated bio-molecular decay to yield hydrogen peroxide and other by-products.

Generated hydroxyl radicals have been found to produce rapid cell death of *Escherichia coli* in natural waters. In addition, the hydroxyl radical has been found to break the carbon-hydrogen bonds. Some twenty five contaminates have been studied, including solvents, aromatics, and pesticides containing nineteen additional compounds. All molecular structures were degraded by the hydroxyl radical. It has also been shown that the hydroxyl radical reacts rapidly with many organic substances in water and is a potential oxidant of refractory synthetic and natural organic compounds that are resistant to degradation by other processes.

The present system uses a combination of electric and magnetic fields to kill bacteria and remove certain chemical contaminants from various fluids. Synergistic effects are obtained by adding air, oxygen, ozone, and/or hydrogen peroxide to the fluid prior to or during its flow through the electric and magnetic fields. The electric and magnetic fields can be applied to the fluid either in sequence or simultaneously. Actual arrangement of the sequences of the application of the electric and magnetic fields and the use and injection locations of synergistic substances will be different depending upon the fluid being treated, the contaminants, and the particular system in which or to which the purification method is applied.

One prior art patent to Bossert, U.S. Pat. No. 5,304,302, is for an apparatus for treating a liquid with alternating magnetic and electric fields. The liquids are treated by passing the liquid through a flow path through a sequence of magnetic fields and a pulsed alternating electrical field. There are also a number of prior patents which utilize either an electric or a magnetic field including the Nathan patent, U.S. Pat. No. 5,738,766, for a device for neutralizing and preventing formation of scale. The descaling device is used to prevent the formation of calcium carbonate in a water conduit by utilizing a electromagnetic coil adjacent the conduit. Similarly, the Larson patent, U.S. Pat. No. 4,865,747, is an electromagnetic fluid treating device which passes a fluid through a non-magnetic conduit having a ferromagnetic core positioned within the conduit for treating the fluid with an electromagnetic field. The Yoshihisa patent, U.S. Pat. No. 4,014,766, is for an electrolytic treatment of waste water. Waste water is subjected to electrolysis in an electrolytic cell so that impurities in the waste water become occluded within a floc of iron hydroxide formed by electrolytic dissolution of iron pieces. A magnetic field can also be applied to the waste water treated electrolytically to promote sedimentation of the floc.

SUMMARY OF THE INVENTION

A liquid decontamination system has a liquid treatment chamber having a liquid input and output and a gas input and output. A plurality of electrodes are positioned to place a voltage across the liquid treatment chamber and the liquid therein. A plurality of magnets are also positioned adjacent the electrodes for placing a magnetic field across the chamber and liquid therein. As the contaminated liquid is fed through the liquid treatment chamber, a predetermined gas, such as nitrogen, ozone, oxygen, or hydrogen peroxide, are fed into the contaminated liquid while simultaneously having the electric and magnetic fields applied to the liquid. The liquid leaving the treatment chamber is fed to a flush tank which removes contaminates and agglomerated solids therefrom.

BRIEF DESCRIPTION OF THE DRAWINGS

Other objects, features, and advantages of the present invention will be apparent from the written description and the drawings in which:

FIG. 1 is a flow diagram of a liquid decontamination system in accordance with the present invention.

DESCRIPTION OF THE PREFERRED EMBODIMENT

Referring to FIG. 1 of the drawings, an electric and magnetic field decontamination system 10 has a liquid treatment chamber 11 and a liquid treatment chamber 12. The liquid treatment chamber 11 has a liquid input 13 having a valve 14 and a liquid output 15 feeding into a flush tank 16. The liquid treatment chamber 11 also has a gas input 17 controlled with a valve 18 which releases the gas into the chamber 20 of the liquid treatment chamber 11. Gas escape lines 21 and 22 each allow gas to escape from the chamber 11. Escape line 21 has a cut-off or control valve 23 while the gas escape line 22 has a control valve 24. The liquid treatment chamber 11 has a first pair of electrodes 25 and 26 and a second pair of electrodes 27 and 28 spaced apart within the liquid flow of the chamber 20. As illustrated in FIG. 1, the pair of electrodes 25 and 26 and 27 and 28 are each in a different polarity in their positioning within the chamber and each is spaced on either side of the chamber to apply an electric voltage or field across the liquid passing through the chamber 20. The electric field can be either a DC or AC type field as desired depending upon the fluid and the contaminant. Also placed in the liquid treatment chamber 11 is a magnet 30 which may be either a permanent magnet or electromagnet and positioned with a predetermined polarity adjacent the electrodes 25 and 26. A second magnet 31 may be a permanent magnet or an electromagnet and is located in the chamber adjacent the electrodes 27 and 28. The magnets 30 and 31 are positioned to provide a magnetic field of generally opposite polarity from each other, as illustrated in the drawing. The liquid leaving the treatment chamber 11 is fed into the flush tank 16 which has a baffle 32 positioned therein to direct the entering liquid from in a downwardly direction towards a flush outlet 33 having a control valve 34. A flushing liquid pipe 35 is also controlled by a shutoff valve 36 and passes through an angled wall 37 in the bottom of the flush tank 16. The end nozzle 38 of the pipe 35 is directed towards the entrance to the flush line 33 so that the fast flowing liquid from the flush input pipe 35 will force flocculate and settling material out the flush line 33 allowing other liquids to pass through the other side of the baffle 22 adjacent the angled wall 37 and into the input 40 of the second liquid treatment chamber.

An output 41 from the liquid treatment chamber 12 feeds into a second flush tank 42. The liquid treatment chamber 12 works on the same principle as the liquid treatment chamber 11 and has a gas inlet pipe 43 distributing a gas within the chamber portion 44. The chamber has electrodes 45 and 46 for producing an electric field across the liquid passing through the chamber. A second set of electrodes 47 and 48 are placed a spaced distance from the electrodes 43 and 45 within the chamber portion 44 and may have a generally opposite polarity from that of the electrodes 45 and 46. A pair of gas outlets 50 and 51 each have a control valve 52 and 53 and are positioned to allow the gas entering the pipe 43 into the chamber portion 44 to escape therefrom after passing through the liquid passing through the treatment chamber 12. A first magnet 54 can be a permanent or electromagnet positioned to put a magnetic field across the chamber 44 through the liquid passing thereby and similarly a second magnet 55, which may be an electromagnet or a permanent magnet, is positioned adjacent the electrodes 47 and 48 and are positioned to place a magnetic field of a polarity which may be generally opposite that of the magnetic field from the magnet 54 through the liquid passing through the treating chamber 12. The flush tank 42 is similar to the flush tank 16 has a downwardly extending baffle 56 dividing the flush tank and directing the liquids from the output 41 to the bottom 57 of the flush tank where they may be expelled through the pipe 58 which is controlled with a control valve 60. The flush input liquid pipe 60 has a control valve 61 enters the angled wall 62 of the flush tank and has its nozzle 63 positioned adjacent the entrance to the flush pipe 58 to force liquids and solids therefrom. The remaining liquid passes around the baffle 56 adjacent the angle wall 62 to an output 64 controlled by an output valve 65.

In operation, the liquid enters the input line 13 through the liquid treatment chamber 11 which has a gas being fed thereto through the pipe 17 which may be any material that enhances the treatment with the electric and magnetic fields. Materials that have been seen to provide a synergistic effect with the electric and magnetic fields in liquid include nitrogen, oxygen, ozone, and hydrogen peroxide. The gas is bubbled through the chamber portion 20 and is then allowed to escape from the escape pipes 21 and 22. The liquid has an electric field from the electrodes 25 and 26 placed on the liquid as the gas is entering the liquid. The liquid passes the first magnetic field 30 and gases through the second electric field between the electrodes 27 and 28 and then passes through the second magnetic field 31. The electric fields created by the electrodes 25 and 26 and those created by electrodes 27 and 28 may be of opposite polarity while the magnetic fields created by the magnets 30 and 31 may also be of opposite polarity to each other.

Treated liquid passing through the treatment chamber has had bacteria and other agent killed and has created hydroxyl ions creating a hydroxyl reaction to breakup the carbon hydrogen bond in some contaminants to break-up contaminants in the liquid including solvents, aromatic hydrocarbons and pesticides. The treated liquid tends to drive the solids and the liquid in the flocculated material to the bottom of the flush chamber 16 where they can be flushed through the pipe 33 by applying of a liquid, such as water, through the pipe 35 while the remaining liquid continues to an output or, as illustrated, into a second treatment chamber 12 which may be identical to the first treatment chamber 11. Contaminated liquids, such as contaminated water, are treated a second time before passing the output into a second flush chamber 42 where the flocculated solids, sludge, and the like are discharged through the discharge pipe 58 and the remaining treated liquid is discharged from the pipe 64.

It should be clear at this time that a system has been provided for treating contaminated liquids, such as contaminated water which both kills the microbiological agent as well as degrades a wide variety of contaminants and which cause a agglomeration of particles into heavier particles which can be flushed from the liquid being treated. It should, however, be clear that the present invention is not to be considered limited to the forms shown which are to be considered illustrative rather than restrictive.

I claim:

1. A liquid decontamination system comprising:

a liquid treatment chamber having a liquid input thereinto and a liquid output therefrom and a gas input thereinto and a gas output therefrom; a first pair of electrodes positioned to place a voltage across said liquid treatment chamber and liquid therein and a second pair of electrodes positioned in a spaced relationship to said first pair of electrodes to place a voltage across said liquid treatment chamber and the liquid therein and a first magnet positioned to place a magnetic field in said chamber and liquid therein at a first magnetic polarity and a second magnet positioned to place a magnetic field in said chamber and liquid therein at a second magnetic polarity whereby a liquid treatment chamber applies a gas to a contaminated liquid passing therethrough simultaneously with spaced electric and magnetic fields; and a flush tank connected to said liquid treatment chamber positioned to receive liquid therefrom, said flush tank having a first output therefrom positioned to direct accumulated materials therefrom and a second output therefrom for discharging treated liquid from said flush tank.

2. A liquid decontamination system in accordance with claim 1 in which flush tank includes a baffle for directing output liquid treatment tank through said fluid tank.

3. A liquid decontamination system in accordance with claim 2 in which flush tank has a flush liquid input positioned to direct a liquid adjacent said flush tank output.

4. A liquid decontamination system in accordance with claim 3 in which said flush tank has an angled wall.

5. A liquid decontamination system in accordance with claim 1 including a second treatment chamber connected to a liquid output from said flush tank, said second treatment chamber having a liquid input thereinto and a liquid output from said second chamber and a gas input into said second chamber and a gas output from said second chamber and a first pair of electrodes positioned to place a voltage across said second liquid treatment chamber and liquid therein and a second pair of electrodes positioned to place a voltage across said second liquid treatment chamber and a first magnet positioned to place a magnetic field in said second chamber and liquid therein and a second magnet positioned to place a magnetic field in said second chamber and liquid therein whereby a liquid treatment chamber applies a gas to said liquid passing therethrough simultaneously with electric and magnetic fields.

6. A liquid decontamination system in accordance with claim 5 including a second flush tank connected to the output of said second liquid treatment chamber.

7. A liquid decontamination system in accordance with claim 6 in which first and second liquid treatment chambers each have a gas control valve thereon to control the gas entering said first and second liquid treatment chambers.

8. A liquid decontamination system in accordance with claim 1 in which said gas input is connected to a nitrogen source.

9. A liquid decontamination system in accordance with claim 1 in which said gas input is connected to a oxygen source.

10. A liquid decontamination system in accordance with claim 1 in which said gas input is connected to an ozone source.

11. A liquid decontamination process comprising the steps of:

selecting a liquid treatment chamber having a liquid input thereinto and a liquid output therefrom and a gas input thereinto and a gas output therefrom; and first and second pairs of electrodes positioned to place a voltage across said liquid treatment chamber through the liquid therein and a first and second magnets positioned to place first and second magnetic fields in said chamber and liquid therein, each said magnet magnetic field having a different magnetic polarity from the other said magnet magnetic field;

feeding a contaminated liquid into said selected liquid treatment chamber;

feeding a gas into said liquid fed into said liquid treatment chamber;

applying an electric field to said contaminated liquid and gas in said liquid treatment chamber;

applying a magnetic field to said contaminated liquid and gas in said liquid treatment chamber;

directed said treated liquid from said liquid treatment chamber into a flush tank; and removing settled materials from said flush tank, whereby a liquid fed into a liquid treatment chamber has a gas applied thereto while being passed through electric and magnetic fields.

12. A liquid decontamination process in accordance with claim 11 in which the step of feeding a gas into said liquid treatment chamber includes feeding nitrogen into said liquid treatment chamber.

13. A liquid decontamination process in accordance with claim 11 in which the step of feeding a gas into said liquid treatment chamber includes feeding oxygen into said liquid treatment chamber.

14. A liquid decontamination process in accordance with claim 11 in which the step of feeding a gas into said liquid treatment chamber includes feeding ozone into said liquid treatment chamber.

* * * * *